(12) United States Patent
Lobel et al.

(10) Patent No.: US 8,029,781 B2
(45) Date of Patent: *Oct. 4, 2011

(54) METHODS OF TREATING A DEFICIENCY OF FUNCTIONAL TRIPEPTIDYL PEPTIDASE I (CLN2) PROTEIN

(75) Inventors: Peter Lobel, Highland Park, NJ (US); David Sleat, Scotch Plains, NJ (US)

(73) Assignee: University of Medicine and Dentistry of New Jersey, Newark, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/881,066

(22) Filed: Sep. 13, 2010

(65) Prior Publication Data

US 2011/0014172 A1 Jan. 20, 2011

Related U.S. Application Data

(63) Continuation of application No. 11/507,945, filed on Aug. 22, 2006, now Pat. No. 7,811,559, which is a continuation of application No. 10/255,317, filed on Sep. 26, 2002, now abandoned, which is a continuation of application No. 09/852,918, filed on May 10, 2001, now abandoned.

(60) Provisional application No. 60/203,407, filed on May 11, 2000.

(51) Int. Cl.
*A61K 38/43* (2006.01)
*A61K 38/16* (2006.01)
*A61K 38/17* (2006.01)
*C07K 14/435* (2006.01)

(52) U.S. Cl. ............ 424/94.1; 514/17.7; 514/21.2; 530/350

(58) Field of Classification Search .................. None
See application file for complete search history.

(56) References Cited

U.S. PATENT DOCUMENTS 6,302,685 B1 10/2001 Lobel et al.

OTHER PUBLICATIONS

Brady et al., *Biochemical Medicine and Metabolic Biology*, 52: 1-9 (1994).
Chang et al., *Molecular Therapy*, 16: 1-8 (2008).
Ezaki et al., *Journal of Neurochemistry*, 72: 2573-2582 (1999).
Hartkainen et al., *Molecular Genetics and Metabolism*, 67: 162-168 (1999).
Lin et al., *Journal of Biological Chemistry*, 276: 2249-2255 (2001).
Lin et al., *Biochemical Journal*, 357: 49-55 (2001).
Rider et al., *Molecular Genetics and Metabolism*, 66: 231-233 (1999).
Schiffmann et al., *Proc. Natl. Acad. Sci. USA*, 97: 365-370 (2000).
Zhong et al., *Clinical Genetics*, 54: 234-238 (1998).

*Primary Examiner* — Christine J Saoud
*Assistant Examiner* — Jon M Lockard
(74) *Attorney, Agent, or Firm* — Jones Day

(57) ABSTRACT

The present invention relates to a method for treating a patient having disorder characterized by a deficient amount of functional CLN2 protein in the affected cells, which comprises administering to the patient an amount of CLN2 protein effective to reduce or eliminate the symptoms caused by the deficiency in CLN2 protein.

19 Claims, 13 Drawing Sheets

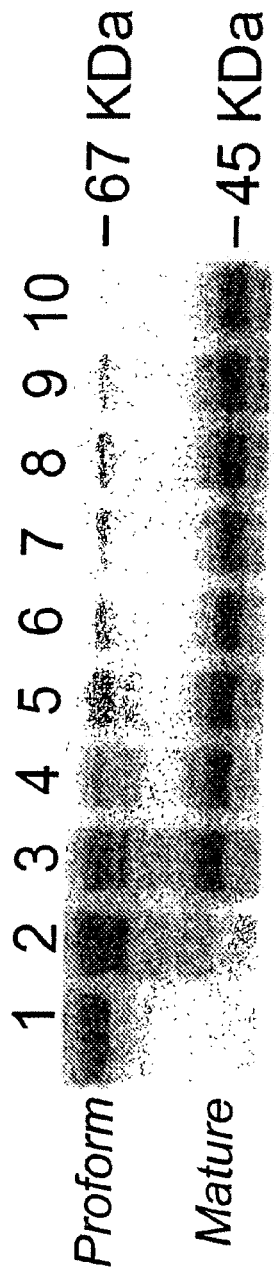
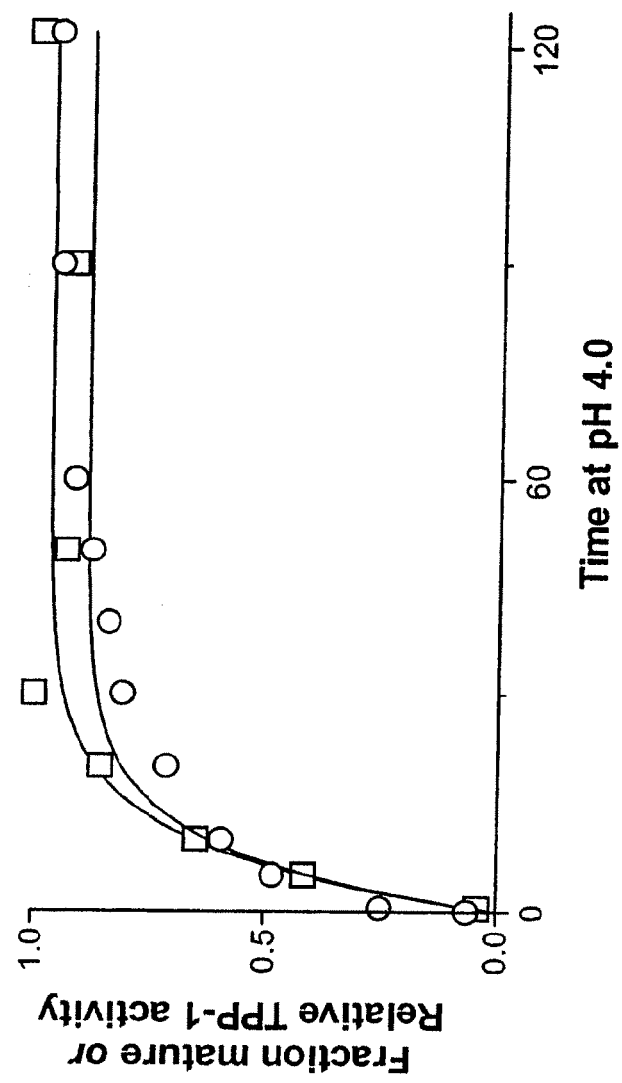
Fig. 7b

METHODS OF TREATING A DEFICIENCY OF FUNCTIONAL TRIPEPTIDYL PEPTIDASE I (CLN2) PROTEIN

CROSS-REFERENCE TO RELATED APPLICATIONS

This application is a continuation of application Ser. No. 11/507,945, filed Aug. 22, 2006, now U.S. Pat. No. 7,811,559, issued Oct. 12, 2010, which is a continuation of application Ser. No. 10/255,317, filed Sep. 26, 2002, now abandoned, which is a continuation of application Ser. No. 09/852,918, filed May 10, 2001, now abandoned, which claims priority to U.S. provisional appl. No. 60/203,407, filed May 11, 2000, all of which are incorporated herein by reference in their entireties.

The research leading to the present invention was supported, at least in part, by NIDDK grant number D K 45992. Accordingly, the government may have certain rights in this invention.

BACKGROUND OF THE INVENTION

The neuronal ceroid lipofuscinoses (NCLs) are a group of closely related hereditary neurodegenerative disorders which affect infants, children and adults, and which occur at a frequency of between 2 and 4 in 100,000 live births. Most forms of NCL afflict children and their early symptoms and disease progression tend to be similar. Initial diagnosis is frequently based upon visual problems, behavioral changes and seizures. Progression is reflected by a decline in mental abilities, increasingly severe and untreatable seizures, blindness and loss of motor skills while further progression can result in dementia or a vegetative state. There is no effective treatment for NCL and all childhood forms are eventually fatal. Several forms of NCL are differentiated according to age of onset, clinical pathology and genetic linkage. These include infantile NCL (INCL, CLN1), classical late infantile NCL (LINCL, CLN2), juvenile NCL (JNCL, CLN3) adult NCL (CLN4), two variant forms of LINCL (CLN5 and CLN6) and possibly other atypical forms.

The CLN2 gene and protein (described in U.S. Ser. No. 08/931,608, filed Sep. 16, 1997, and Sleat et al. (1997) Science 277:1802-1805), when mutated, result in the autosomal recessive disease classical late infantile neuronal ceroid lipofuscinosis (LINCL, OMIM 204500). CLN2 encodes the protein lysosomal enzyme tripeptidyl peptidase I (also called CLN2 protein, CLN2 gene product, TPP-I, EC3.4.14.9) (Sleat et al., Vines and Warburton (1999), FEBS Lett. 443 131-135) which is a 46 kDa lysosomal protein that is absent or mutated in LINCL. In its absence, storage material whose major identifiable component is mitochondrial ATP synthase subunit c accumulates in the lysosomes of affected patients in neurons and other cell types (Palmer et al. (1995) Am. J. Med. Genet. 57:260-265). There is a need to develop therapeutic applications, based on CLN2, for treatment of LINCL and related diseases. Currently, there is no effective treatment for the disease and death typically occurs between ages 6 and 15 (Mole (1998) Neurobiol. Dis. 5:287-303).

Enzyme replacement therapy is a desirable treatment for lysosomal storage diseases such as LINCL that are characterized by a deficient amount of functional CLN2 protein in the affected cells. In enzyme replacement therapy recombinant (or natural) enzyme is administered to the affected cells to correct the metabolic defect, an approach that has proven successful for Gaucher's disease. Administration of glucocerebrosidase has proved remarkably effective in treating many patients with Gaucher's disease (Brady, R. O. and Barton, N. W. (1994) Biochem Med Metab Biol 52, 1-9), and there are clinical trials ongoing for a number of other lysosomal storage disorders (Schiffmann et al. (2000) Proc Natl Acad Sci U S A 97, 365-370; Bijvoet et al. (1999) Hum Mol Genet 8, 2145-2153; Chen, Y. T. and Amalfitano, A. (2000) Mol Med Today 6, 245-251; Downs-Kelly et al. J. Mol. Neurosci. (2000); Kaye (2001) in Current Treatment Options in Neurology 3:249-256; Kakkis et al. (2001) Mol. Genet. Metab. 72:199-208; Byers et al. (2000) Pediatr. Res. 47:743-749; Brady and Schiffman (2000) JAMA 284:2771-2775; Vogler et al. (1999) Pediatr. Res. 45:838-844; Zirzow et al. (1999) Neurochem. Res. 24:301-305; Platt and Butters ((1998) Biochem. Pharmacol. 56:421-430; Crawley et al. (1997) J. Clin. Invest. 99:651-662; Brady and Barton (1997) Lipids March 31 Suppl. S137-139; Barton et al. (1993) New Eng. J. Med. 328:1564, 1567, 1568).

SUMMARY OF THE INVENTION

It is the object of the invention to provide a therapy by which a patient having disorder characterized by a deficient amount of functional CLN2 protein in the affected cells can be treated by administering to the patient an amount of CLN2 protein effective to reduce or eliminate the symptoms caused by the deficiency in CLN2 protein.

Panel A. Recombinant human CLN2 protein produced from CHO cells was maintained in phosphate buffered saline or diluted into 150 mM NaCl/50 mM formate pH 3.5 buffer and incubated 16 hours at 37 C. Samples were applied to a reducing denaturing gel (Novex NuPAGE bis-tris gel with MES running buffer) and proteins visualized by Coomassie blue staining. The size of the prestained molecular weight standards shown in the left lane are listed according to the corrected molecular weight assigned by the supplier (Novex).

Panel B. Recombinant human CLN2 protein produced by insect cells in 150 mM NaCl/20 mM Tris pH8/0.2% Tween 20 was diluted into acid buffer (150 mM NaCl/0.1% triton X-100/sodium acetate pH 4.0) at room temperature. Samples were diluted into SDS-PAGE buffer, separated on a 10% SDS-PAGE gel (Novex) and analyzed by silver staining (top panel). Lane 1 represents the zero time point (sample diluted directly into SDS-PAGE sample buffer without exposure to acidic conditions) while lanes 2 to 10 represent samples taken 0.5, 5, 10, 20, 30, 40, 50, 60, 90, and 122 minutes after dilution into acid buffer. The size of the molecular weight standards is indicated on the right. The gels were scanned and conversion to mature form calculated (intensity of lower band normalized to the sum of the intensities of the upper and lower bands) (graph, open circles). Samples were also diluted into TPP-I assay buffer and the initial rate of substrate hydrolysis determined (graph, square symbols). The purified CLN2 protein used in this experiment differed from that produced in CHO cells in that it contained a C-terminal hexahistidine tag. This, plus differences in glycosylation, is responsible for the slightly different apparent molecular weights of the two preparations. However, the amino terminus of the pro and mature CLN2 protein from the two preparations were identical.

Figure 8:
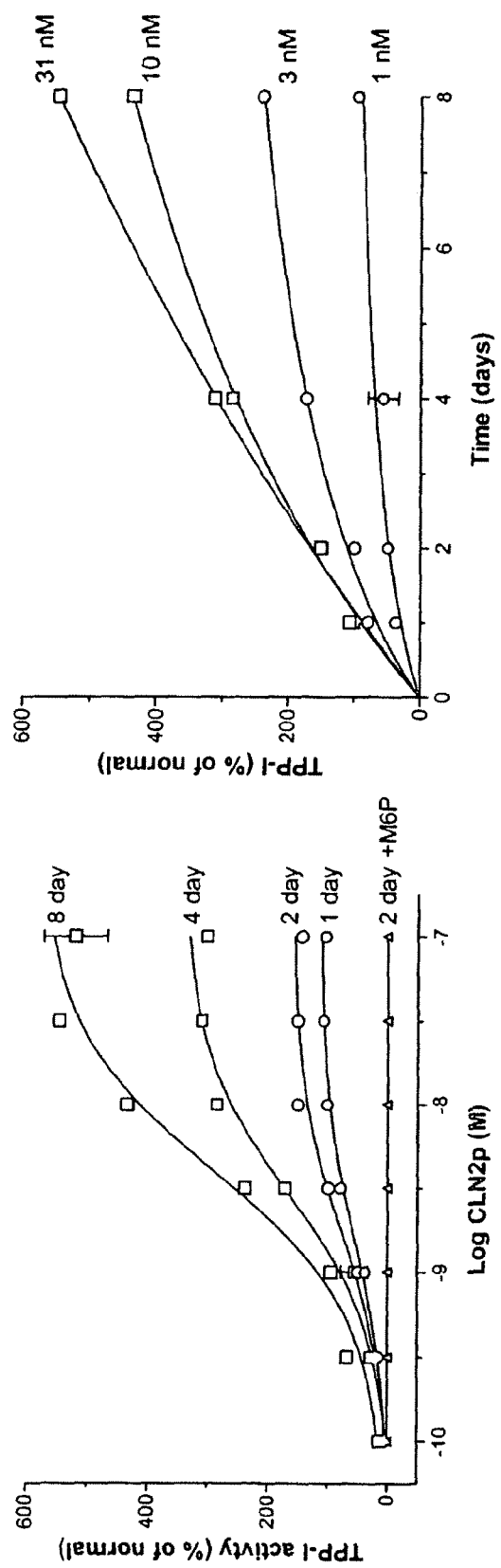

FIG. 8. Uptake of recombiant human CLN2 protein by LINCL fibroblasts. Confluent LINCL fibroblasts in 48 well plates were incubated with 1 ml RPMI1640/10% FBS containing the indicated concentrations of anion exchange and gel filtration purified proCLN2 protein. Where indicated, the medium also contained 10 mM mannose 6-phosphate. At the indicated times, cells were rinsed 3 times with phosphate buffered saline and lysed with 1% nonidet P-40/150 mM NaCl/10 mM Tris pH 7.5 at 4 C. Lysates were assayed for TPP-I activity. Activity is normalized to wells plated with a normal control fibroblast.

Figure 9:
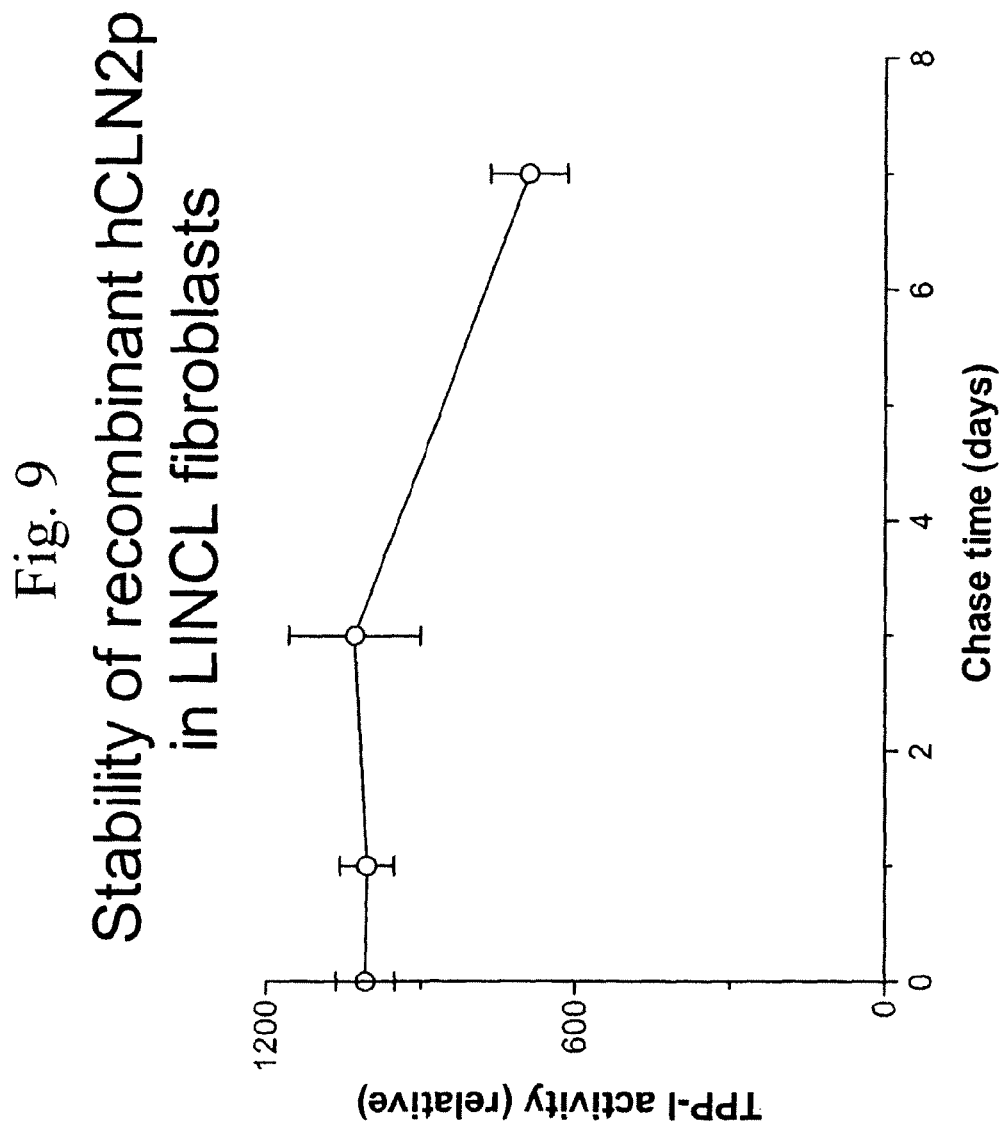

FIG. 9. Stability of recombinant human CLN2 protein in LINCL fibroblasts. Cells were incubated with either 10, 31, or 100 nM proCLN2 protein for 24 hours as described in FIG. 8. Media were removed and cells were rinsed once with RPMI1640/10% FBS. Fresh RPMI1640/10% FBS was added and the incubation conditioned for 1, 3, or 7 days and the cells processed as described in FIG. 8.

Figure 10:
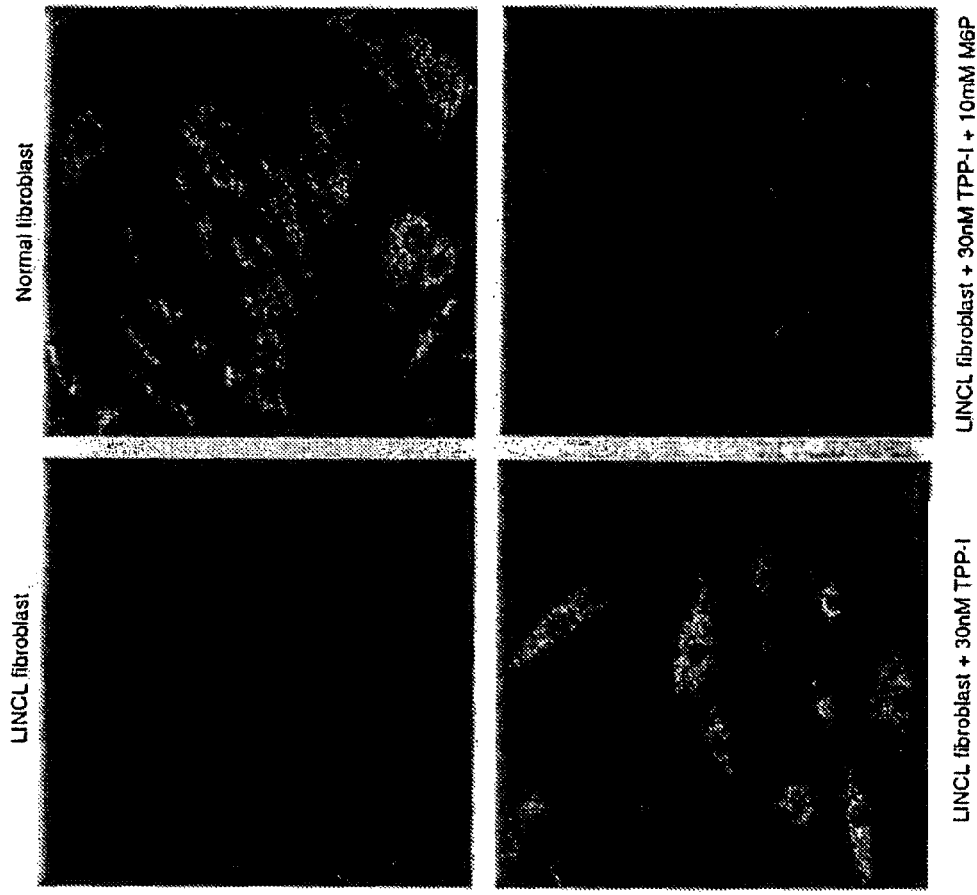

FIG. 10. Immunofluorescence detection of CLN2 in normal and LINCL fibroblasts. LINCL cells were plated onto coverslips and cultured in growth medium (RPMI1640/10% FBS) alone or with 32 nM CLN2 protein in the presence or absence of 10 mM mannose 6-phosphate. Cells were fixed in Bouin's fixative, permeabilized with 0.5% Triton X-100/phosphate buffered saline, blocked with blocking buffer (3% BSA/0.2% Tween 20/500 mM NaCl/phosphate buffered saline), and incubated with rabbit anti-CLN2 protein antisera (1:100 dilution in blocking buffer). Bound antibody was detected using FITC-goat anti rabbit antibodies. Normal control cells grown in RPMI1640/10% FBS were probed in parallel.

Figure 11:
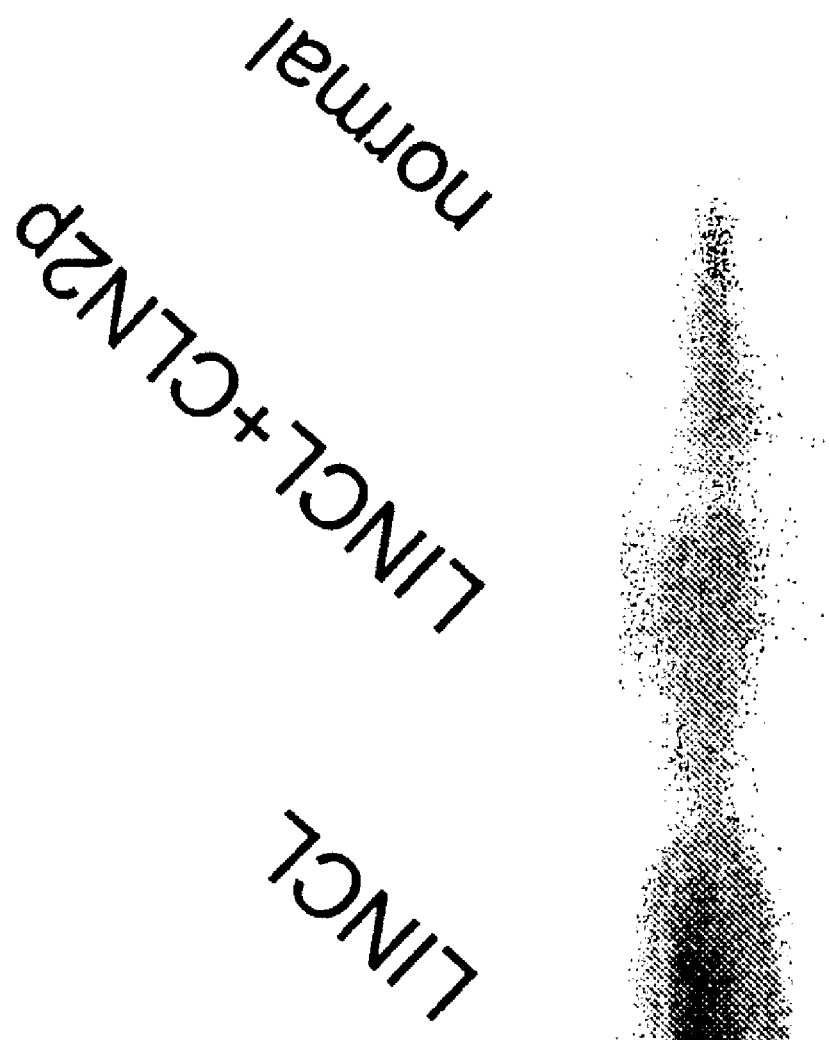

FIG. 11. Mitochondrial ATP synthase subunit c in normal and LINCL fibroblasts. Confluent fibroblasts were cultured in RPMI 1640/10% FBS, containing 30 nM CLN2 protein where indicated, for 7 days. Cells were solubilized in lithium dodecyl sulfate sample buffer and proteins separated by SDS-PAGE on precast NuPAGE 10% Bis-Tris gel using MES running buffer (Invitrogen). Western blotting was conducted using rabbit antibodies against mitochondrial ATP synthase subunit c [4] and enhanced chemiluminescence (Renaissance, NEN).

Figure 12:
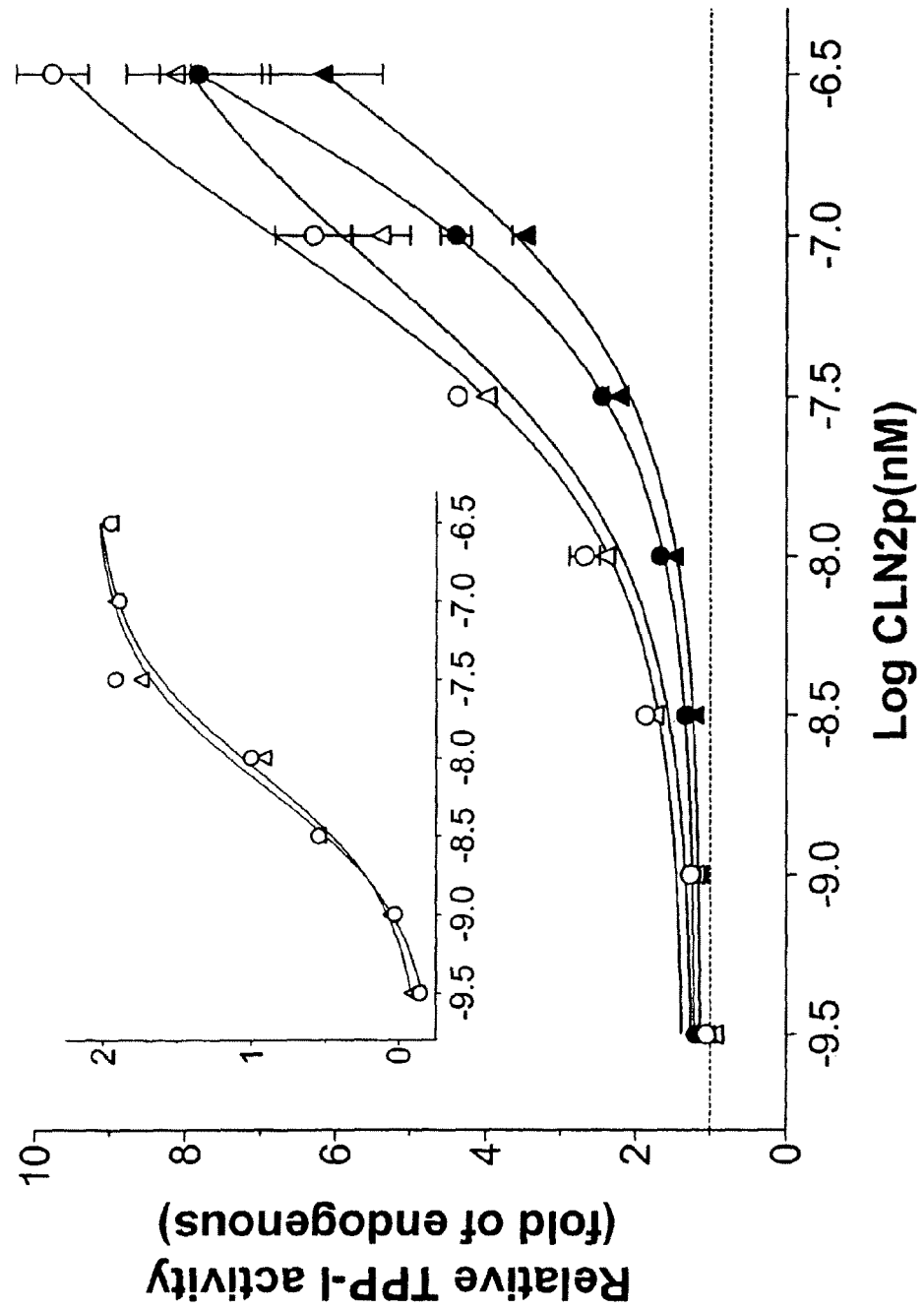

FIG. 12. Uptake of recombinant CLN2 protein by rat cerebellar granule neurons. Cerebellar granule neurons were cultured in 48-well plates for one day in medium containing the indicated concentrations of CLN2 protein in the presence (filled symbols) or absence (open symbols) of 10 mM M6P. Cells were lysed as described in Experimental Procedures and then assayed for TPP-I activity using the kinetic assay (see FIG. 3) after a 30 minute preincubation at 37° C. in pH 3.5 buffer to activate proenzyme (circles) or at 0° C. in pH 7.5 buffer to prevent proenzyme activation (triangles). Dotted line represents the endogenous TPP-I activity level. Data represent the mean±standard error of triplicate determinations. Data were fit to sigmoidal dose-response model using Prism 3.0. The inset shows the difference between the activity associated with the cells incubated in the absence and presence of M6P, with the circles representing preactivated samples and the triangles representing non-preactivated samples.

DETAILED DESCRIPTION OF THE INVENTION

The subject invention is directed to a method for treating a patient having disorder characterized by a deficient amount of functional CLN2 protein in the affected cells by administering to the patient an amount of CLN2 protein effective to reduce or eliminate the symptoms caused by the deficiency in CLN2 protein. Alternatively, the amount of CLN2 protein administered may be such that normal levels of CLN2 protein in the cell are restored.

A patient in whom administration of CLN2 is an effective therapeutic regimen is preferably a human, but can be any animal. Thus, as can be readily appreciated by one of ordinary skill in the art, the methods and pharmaceutical compositions of the present invention are particularly suited to administration to any animal, particularly a mammal, including, but by no means limited to, domestic animals, such as feline or canine subjects, farm animals, such as but not limited to bovine, equine, caprine, ovine, and porcine subjects, wild animals (whether in the wild or in captivity), research animals, such as mice, rats, rabbits, goats, sheep, pigs, dogs, cats, etc., avian species, such as chickens, turkeys, songbirds, etc., i.e., for veterinary medical use.

In such a disorder, certain cells of the patient do not have sufficient functional CLN2 protein. By functional is meant that the CLN2 protein may, for example, be absent, or inactive, or present in inadequate levels. The disorder may be determined by taking samples of various cell types and detecting by known methods whether the CLN2 protein is not being expressed or is otherwise not functional as defined. Such methods may include enzyme activity assays, microscopy, immunofluorescence, and nucleic acid hybridization (using for example proteins and nucleic acids described in U.S. Ser. No. 08/931,608 and Sleat et al. (1997)). The affected cells may belong to any cell or tissue type, but are preferably neurons. The presence of such a disorder may also be detected by physical symptoms such as seizures and loss of motor skills.

Preferably the disorder is characterized by accumulation of one or more storage products in the lysosomes of the affected cells, in particular neurons. One mode of determining the disorder is finding that the lysosomes have accumulated storage material, which can be done by known methods such as microscopy or immunofluorescence. An example of a storage material which would be detected in lysosomes is mitochondrial ATP synthase subunit c. Successful treatment with CLN2 protein will reduce or eliminate mitochondrial ATP synthase, in particular subunit c in the lysosomes of the affected cells, such as neurons. Detecting elimination of storage material such as mitochondria ATP synthase subunit c in the lysosomes of affected cells can be done by known methods as described above. An example of such a disorder is LINCL.

The CLN2 protein may be in an inactive proenzyme (or prodrug) form, or in the shorter active form. Either of these may be naturally isolated, or recombinant. When produced for example in Chinese hamster ovary (CHO) cells, CLN2 protein in its proenzyme form is obtained. This form converts to the active form following acidification. Therefore the proenzyme is a highly suitable prodrug which remains inactive until delivered to lysosomes, whose acidic environment will activate it. Obtaining CLN2 protein in any of these forms is described in detail below and in U.S. Ser. No. 08/931,608 and Sleat et al. (1997). Briefly, CLN2 protein is isolated using known methods from human brain samples by purifying mannose-6-phosphate containing glycoproteins from normal and LINCL brain samples and isolating the protein band present in the normal but not in the LINCL specimens. Once the protein is obtained, the corresponding gene and cDNA are also isolated using known methods. Recombinant protein is then produced from the cDNA using known methods. The CLN2 protein in any of the above forms may or may not be mannose-6-phosphorylated.

The CLN2 protein may be used alone or with other active ingredients. It may be conjugated to a polyalkylene glycol moiety by known methods, or may be used as part of a chimeric protein, for example as linked to an antibody or parts thereof, a transferrin, a hormone, or a growth factor. The CLN2 protein may be provided in the form of a prodrug, i.e. a stable inactive form that becomes active once it is administered (for example as described above). The instant invention provides for conjugating targeting molecules to CLN2, DNA vectors (including viruses) encoding CLN2, and carriers (i.e., liposomes) for targeting to a desired cell or tissue, e.g., the brain. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a protein or peptide ligand of an internalized receptor on the target cell. In a specific embodiment, the targeting molecule is a peptide comprising the well known RGD sequence, or variants thereof that bind RGD receptors on the surface of cells such as cancer cells, e.g., human ova that have receptors that recognize the RGD sequence. Other ligands include, but are not limited to, transferrin, insulin, amylin, and the like. Receptor internalization is preferred to facilitate intracellular delivery of CLN2 protein. In another embodiment, the targeting molecule is an antibody. Preferably, the targeting molecule is a monoclonal antibody. In one embodiment, to facilitate crosslinking the antibody can be reduced to two heavy and light chain heterodimers, or the $F(ab)_2$ fragment can be reduced, and crosslinked to the CLN2 via the reduced sulfhydryl. Antibodies for use as targeting molecule are specific for cell surface antigen. In one embodiment, the antigen is a receptor. For example, an antibody specific for a receptor on cancer cells, such as melanoma cells, can be used. This invention further provides for the use of other targeting molecules, such as lectins, carbohydrates, proteins and steroids.

The CLN2 protein may be administered in a composition with pharmaceutically acceptable carriers and/or excipients. The phrase "pharmaceutically acceptable" refers to molecular entities and compositions that are physiologically tolerable and do not typically produce an undesired reaction, such as gastric upset, dizziness, allergic reactions and the like, when administered. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans, although a pharmaceutically acceptable carrier of the invention may share the attributes of such an approved carrier without itself having been approved. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition of this invention preferably includes an uptake inhibitor which decreases local clearance of CLN2 protein by cell surface receptors. This helps ensure that the CLN2 protein is administered evenly, such that more cells get some CLN2 protein, rather than the few cells close to the site of administration getting most of the CLN2 protein. Clearance mechanisms include endocytosis by cell surface receptors such as the mannose receptor, the asialoglycoprotein receptor, and the mannose-6-phosphate receptor. Thus a preferred uptake inhibitor is mannose-6-phosphate. The uptake inhibitor can be administered in a composition with CLN2 protein, or can be separately but simultaneously administered, or the two can be administered at different times as long as the uptake inhibitor is able to have the desired effect.

An amount of CLN2 protein effective to reduce or eliminate the symptoms caused by the deficiency in CLN2 protein is readily determined by the skilled practitioner. As discussed above, alleviation (i.e. reduction or elimination) of symptoms may be determined based on the physical condition of the patient, for example cessation of seizures or reduction in amount or intensity of seizures. Or the measurement may be made on cell samples, for example brain neurons, by determining the amount of storage products present in lysosomes and comparing with normal control cells to confirm relief of the condition. Thus the dosage may be determined by a skilled practitioner depending on the age, size, and condition of the patient. Alternatively, the amount of CLN2 protein administered may be such that normal levels of CLN2 protein in the cell +are restored, as determined for example by comparison to normal cells. In a preferred treatment, the effective amount of CLN2 protein is such that the affected cells receive from about 1.0 nM to about 100 nM of CLN2 protein. The dosage used to ensure the affected cells receive from about 1.0 to 100 nM of CLN2 protein may be determined by the skilled practitioner, for example by a biopsy after administration and analysis of treated cells by known methods to determine how much injected or oral or inhaled (for example) CLN2 is required to provide the desired cell levels. When administered with an uptake inhibitor, the uptake inhibitor should be at a concentration that would inhibit immediate clearance of the CLN2 protein near the site of administration. Such a dosage may be determined by a skilled practitioner. When the uptake inhibitor is mannose-6-phosphate, 5 mM is a preferred dosage.

According to the invention, the CLN2 protein or a composition including the CLN2 protein may be introduced parenterally, transmucosally, e.g., orally, nasally, or rectally, or transdermally. Preferably, administration is by injection, especially parenteral, e.g., via intravenous injection, and also including, but is not limited to, intra-arteriole, intramuscular, intradermal, subcutaneous, intraperitoneal, intraventricular, and intracranial administration.

CLN2 protein or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid). To reduce its systemic side effects and increase cellular penetration, this may be a preferred method for introducing CLN2.

CLN2 protein or composition can be delivered in a controlled release system. For example it may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site LINCL-affected tissue. Other controlled release systems are discussed in the review by Langer (Science 249:1527-1533 (1990)).

The examples which follow are illustrative and are not intended to limit the invention. Various modifications of the invention in addition to those described herein will become apparent to those skilled in the art from the foregoing description and the accompanying figures. Such modifications are intended to fall within the scope of the invention and the appended claims.

EXAMPLES

Plasmid Construction, Cell Selection, and Gene Amplification

CHO cells were transfected with PvuI linearized pMSXND1 CLN2 (a fragment corresponding to nucleotides 1-1707 of human CLN-2 cDNA (Genbank Accession No. AF017456, 175 Arg variant) in the expression vector pMXNS [8]) using the lipofectamine procedure (Gibco). Stable transfectants were isolated by selection with 700 microgram/ml G418 and individual colonies isolated using cloning cylinders. Select colonies were treated with 0.2 micromolar MTX in α-MEM without nucleotides/10% dialyzed FBS to select for cells that had undergone gene amplification. When cells became resistant, the MTX concentration was increased and the procedure repeated. After twelve cycles of selection, cells resistant to 400 micromolar methotrexate were obtained.

Enzyme Assay

The TPP-I activity assay was conducted using a modification of the method of Vines and Warburton (Biochem. Biphys. Acta. 1998 1384 pp 233-42). Unless indicated otherwise, samples were preincubated in 150 mM NaCl/0.1% triton X-100/50 mM formate pH 3.5 for 30 minutes at 37 C to convert proCLN2 to active enzyme.

Production of Recombinant CLN2 Protein in CHO Cells.

Figure 1:
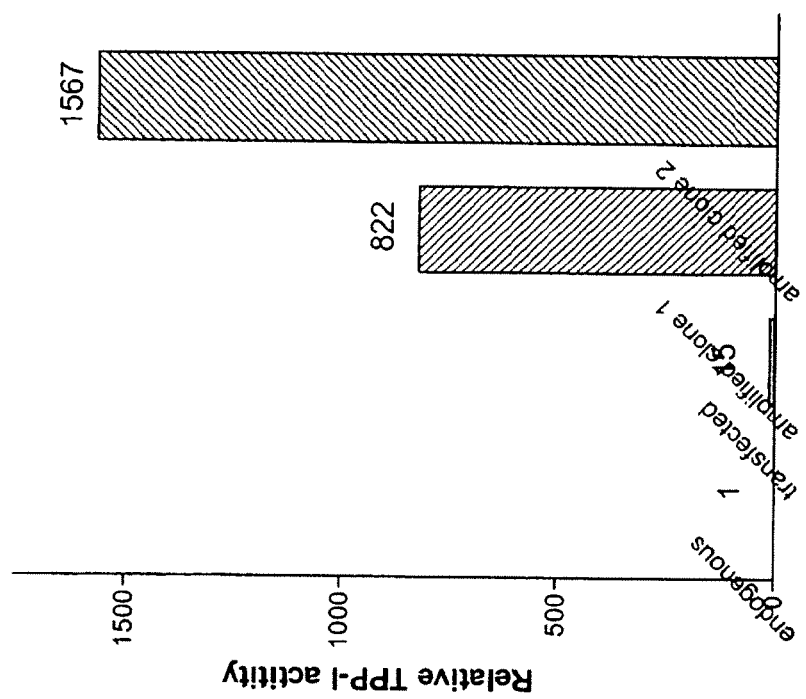
FIG. 1. Comparison of CLN2 protein expression level in CHO cells. Adherent cells were grown to confluency in DMEM/F12 containing 10% FBS. Media were replaced with serum free DME/F12 on day 0. Conditioned media were collected on day 2 and assayed for TPP-I activity after acidification to convert proCLN2 protein to active enzyme.

Full-length human CLN2 cDNA was cloned into pMSXND1 vector (S-J Lee and D Nathans, 1988 J. Biol. Chem. 263 3521-7). The resulting plasmid contains a CLN2 expression cassette driven by the metallothione I promoter, a neomycin-resistance cassette for G418 selection, and a dihydrofolate reductase expression cassette for methotrexate (MTX) resistance. CHO cells were transfected with linearized plasmid using lipofectamine (Gibco) and stably transfected clones were isolated after G418 selection. The TPP-I activity in conditioned medium was assayed and the highest expressor was treated with MTX to select for clones that had undergone gene amplification. The TPP-I activity level in conditioned medium was increased by 15 fold over endogenous level after transfection and G418 selection and further increased to >1000-fold over untransfected cells after MTX amplification (FIG. 1).

Figure 2:
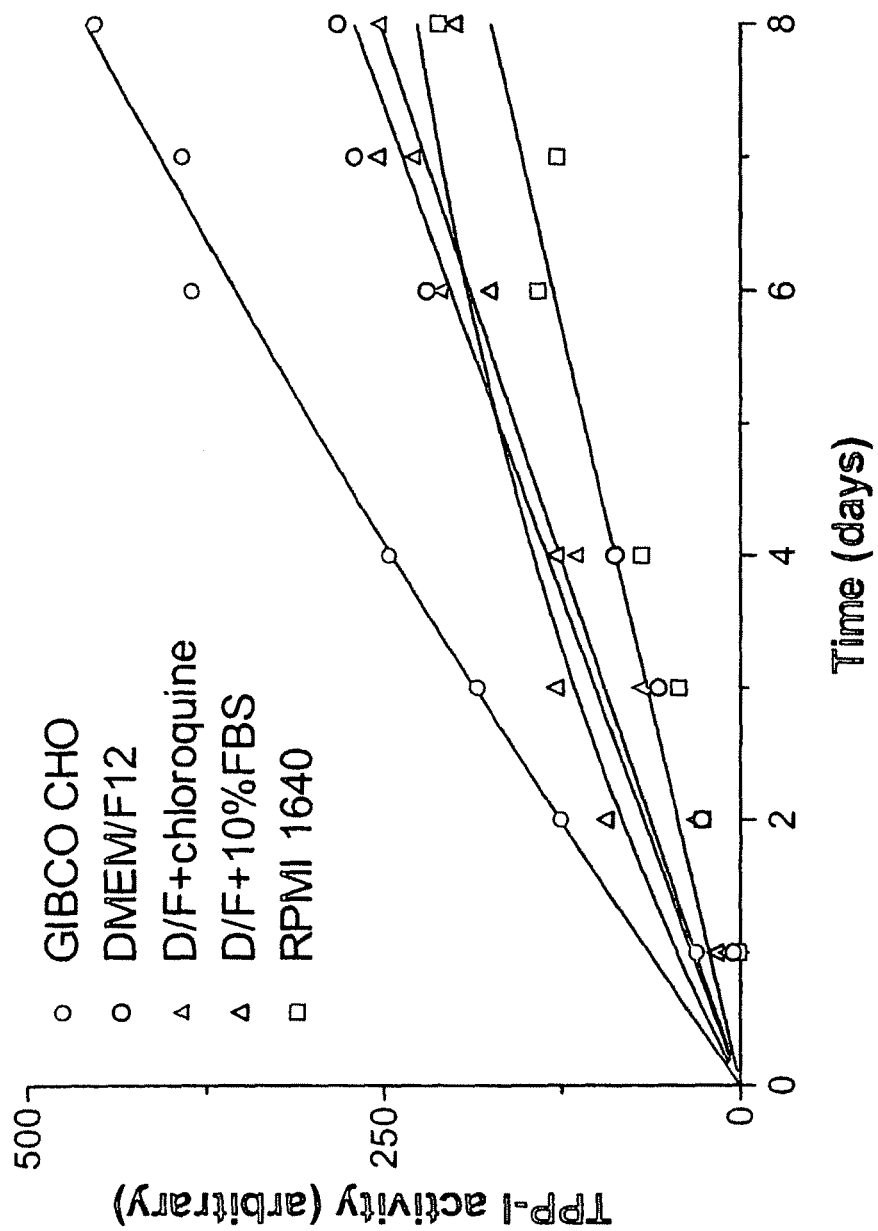
FIG. 2. Comparison of CLN2 protein secretion in different culture media. Adherent cells in 6-well plates were grown to confluency in DMEM/F12 containing, 10% FBS. Media were replaced with 5 ml of the indicated culture media on day 0 and 0.1 ml removed for enzyme activity measurements as indicated.

Culture conditions were evaluated in an attempt to optimize the production system. We compared various growth media including different types of standard media with or without fetal bovine serum, reduced serum medium, and specialized low-protein formulations for CHO cell. A representative experiment is shown in FIG. 2. Gibco CHO—S—SFM II media resulted in the best yield. However, this media contains protein components that could interfere with downstream purification. Thus, even though the protein-free medium DMEM/F12 gave approximately a two-fold lower yield, we chose to use this medium for production purposes.

Figure 3:
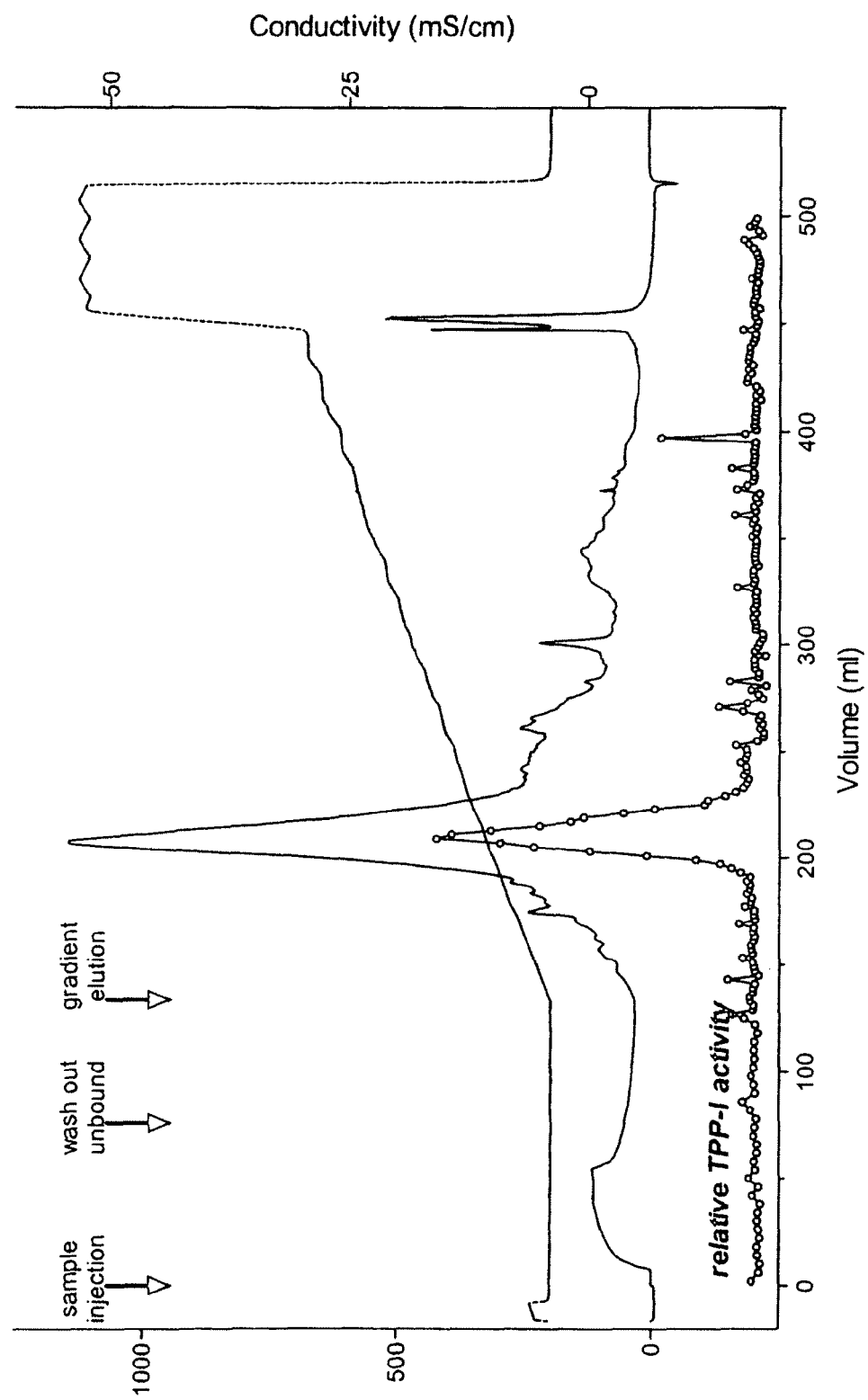
FIG. 3. Anion exchange chromatography of recombinant CLN2 protein. Material from 12 150 $cm^2$ dishes containing confluent adherent CHO cells that overexpress CLN2 protein were cultured for 8 days in DMEM/F12 (82 ml/well). Media were removed, filtered through a 0.2 micron cellulose acetate membrane, and placed in a stirred cell apparatus equipped with a YM-30 membrane (Amicon). The sample was concentrated and the buffer exchanged to 50 mM NaCl/20 mM Tris pH 8.0 to a final volume of 40 mL. The sample was applied to a 15×68 mm UnoQ 12 column at a flow rate of 2 ml/min. The column was washed with 50 mM NaCl/20 mM Tris pH 8.0 and eluted with 40 column volumes of a linear gradient of 50 to 525 mM NaCl. Fractions (4 ml during load and wash, 2 ml during gradient elution) were collected and analyzed for TPP-I enzyme activity. The pooled fractions eluting from 200-225 ml contained 17 mg proCLN2 as calculated from the OD280 using an extinction coefficient of 1.345 ml/mg/cm. Chromatography was conducted at 4 C using an Akta Explorer system (Amersham Pharmacia).
Figure 4:
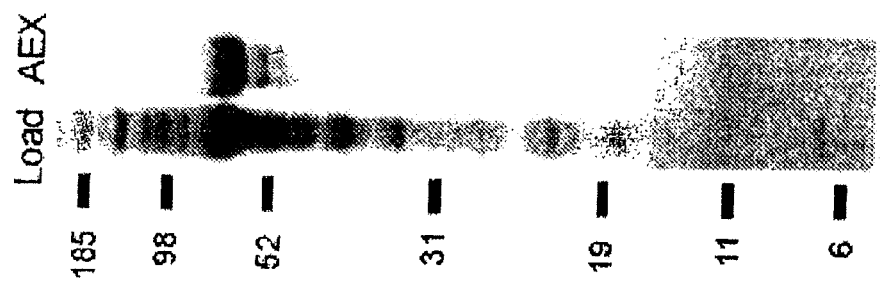
FIG. 4. Gel electrophoresis of transfected CHO cell conditioned media before and after anion-exchange chromatography. The lanes labeled "Load" and "AEX" represent 7.5 microliters of the 40 ml starting material and the 2 ml peak fraction eluting at 208-209 ml, respectively, of the anion exchange column depicted in FIG. 3. The gels (10% NuPAGE, Novex) were stained with Coomassie brilliant blue.

Purification and characterization of recombinant CLN2 protein. CHO cell culture medium was concentrated by ultrafiltration through YM-30 membrane and buffer exchanged into low salt solution. The material was subjected to anion-exchange chromatography on a Uno Q12 column (BioRad). The TPP-I activity profile reveals that the CLN2 protein represents the major OD280 peak that elutes at about 150 mM NaCl (FIG. 3). Comparison of the proteins present in the source material and the peak anion exchange fractions by denaturing PAGE (10% NuPAGE, Novex) and Coomassie blue staining indicates that the 65 KDa CLN2 protein is the major protein in the conditioned media and that most minor components are removed by ion exchange chromatography (FIG. 4).

Figure 5:
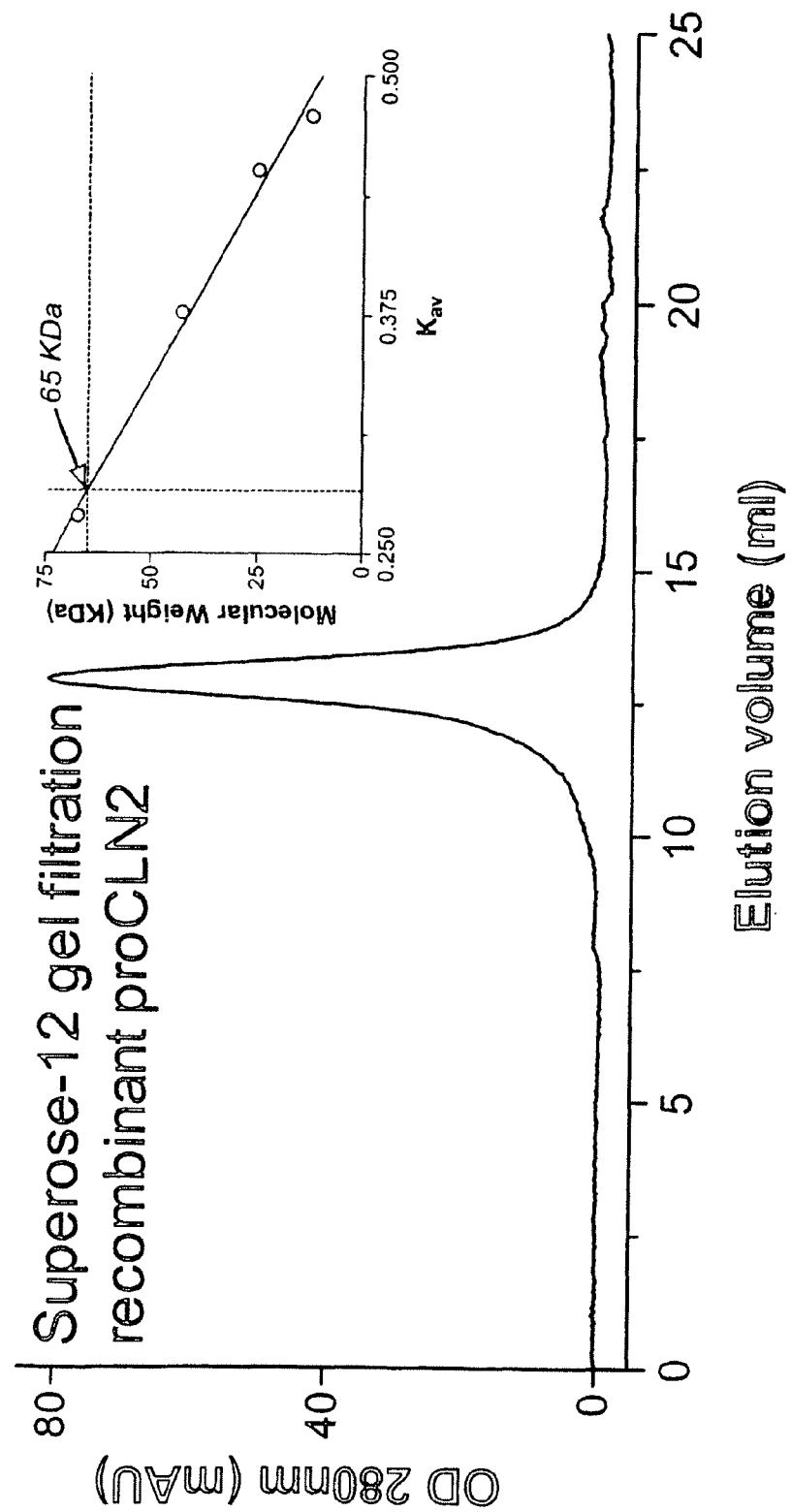
FIG. 5. Analytical gel filtration of proCLN2 protein. Anion-exchange purified proCLN2 (0.14 ml of 0.59 mg/ml protein) was applied to a Superose 12 HR 10/30 column (Pharmacia). The column was eluted at a rate of 0.5 ml/min with phosphate buffered saline. The column was calibrated under the same conditions using blue dextran to determine the void volume and the globular protein standards bovine serum albumin (67 KDa), chicken ovalbumin (43 KDa), chymotrypsinogen (28 KDa), and cytochrome c (12.4 KDa).

Peak fractions were pooled and applied to a Superose-12 gel filtration column. The protein elutes as a single peak that, in comparison to gel filtration standards, elutes as a globular protein of 65 kDa (FIG. 5). This indicates that the CLN2 protein precursor exists as a monomer in solution at pH7.4. Note that all chromatography was performed at slightly alkaline pH (pH 7.4 to 8.0) as the inactive CLN2 precursor undergoes autoactivation to active 46 Kda CLN2 protein at acidic pH (see below).

Figure 6:
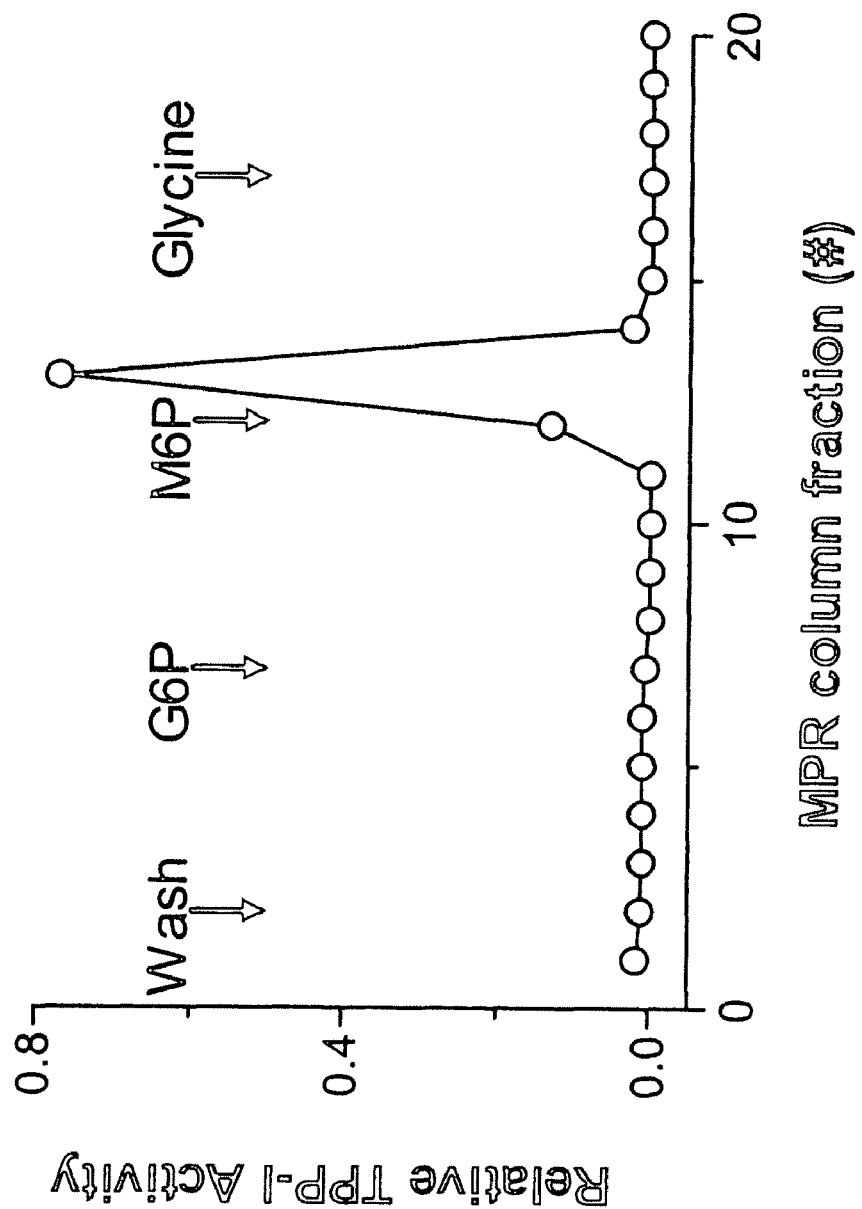
FIG. 6. Mannose 6-phosphate receptor chromatography of proCLN2 protein. The sample (0.2 ml of 0.58 mg/ml anion-exchange purified proCLN2 protein) was applied to a 1.5 cm$^3$ affigel 10 (BioRad)-immobilized soluble cation-independent mannose 6-phosphate receptor (~2.5 mg receptor/cm$^3$ resin). The column was washed with 5×1.5 ml Buffer A (phosphate buffered saline containing 0.2% tween-20 and 5 mM β-glycerophosphate), 5×1 ml Buffer A containing 100 mM glucose 6-phosphate, 5×1 ml Buffer A containing 10 mM mannose 6-phosphate, and 4×1 ml 0.1 M glycine pH 2.5. Fractions were analyzed for TPP-I activity.

Ideally, the recombinant CLN2 protein used for enzyme replacement therapy should contain mannose 6-phosphate to allow its endocytosis and delivery to the lysosome. To investigate its mannose 6-phosphorylation state, recombinant proCLN2 was applied to a column of immobilized soluble cation-independent mannose 6-phosphate receptor. The column was washed with column buffer, column buffer containing glucose 6-phosphate (which does not bind to the mannose 6-phosphate receptor and potentially could release some non-specifically bound material), mannose 6-phosphate, and glycine buffer (to elute tightly or non-specifically bound material). The fractions were analyzed by the TPP-I activity assay after autoactivation (FIG. 6) or by SDS-PAGE (data not shown). Essentially all of the CLN2 protein was retained on the column and was specifically eluted with mannose 6-phosphate. This demonstrates that recombinant CLN2 protein produced in CHO cells is mannose 6-phosphorylated.

Figure 7A:
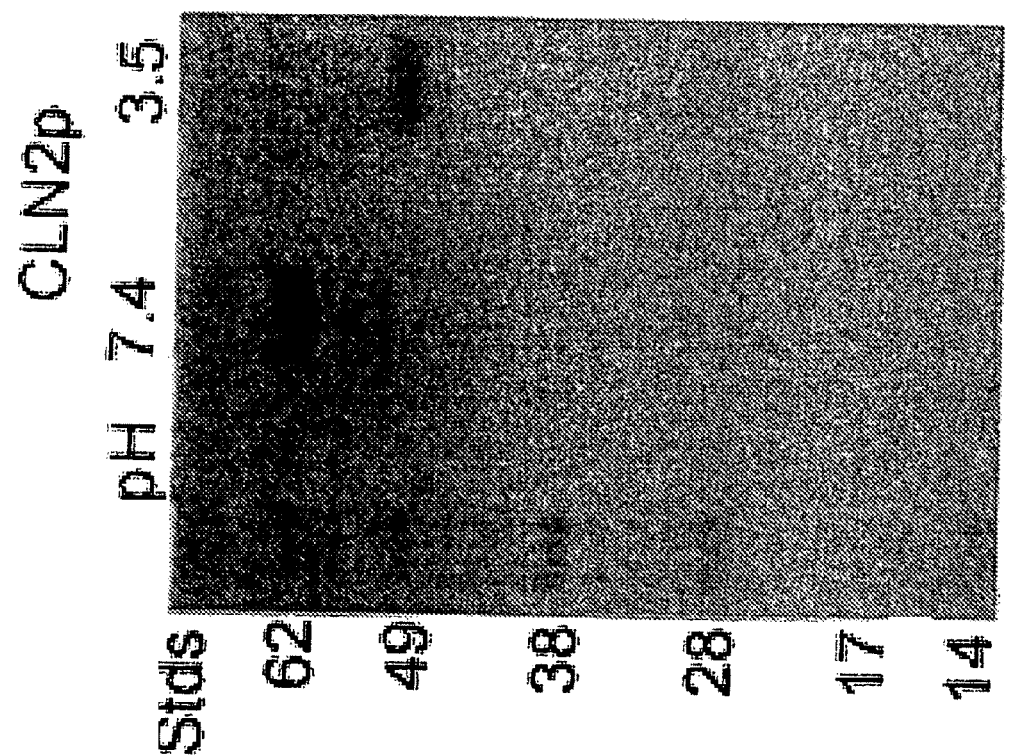
FIG. 7. Autoactivation of recombinant human CLN2 protein.

Autocatalytic processing of CLN2 protein/TPP-I. When maintained at neutral or alkaline pH, purified CHO-cell produced human recombinant CLN2 protein has an apparent size of about 65 KDa by denaturing PAGE (FIGS. 4 and 7a). Edman degradation revealed that the amino terminus (SYSPE . . . ) corresponds to residue 20 of the translated CLN2 message. This indicates that CLN2 protein is synthesized as a preproprotein whose signal sequence is cleaved after residue 19 to generate proCLN2 protein. Upon incubation at acidic pH the 65 KDa protein is converted to a 46 KDa species whose amino terminus (LHLGV) corresponds to residue 196 of the translated CLN2 message. This amino terminus is identical to endogenous CLN2 protein isolated from human brain (Sleat et al 1997, Science 277 pp 1802-1805). Kinetic analysis of highly purified recombinant CLN2 protein produced in insect cells indicate that the proteolytic processing is accompanied by acquisition of enzymatic activity (FIG. 7b). (Note that the CHO cell preparation is used for all other experiments described in this application. The insect cell preparation was used for this analysis before the CHO cell preparation was available. Preliminary experiments indicate that with respect to autocatalytic processing, the two preparations are essentially identical). These data indicate that the CLN2 protein is synthesized as an inactive proenzyme and upon acidification undergoes autolysis to an enzymatically active species.

Uptake of CLN2 protein by LINCL fibroblasts. We performed proof of principle experiments to determine if recombinant CLN2 protein could be targeted to LINCL cells. Confluent LINCL fibroblasts were incubated with increasing concentrations of purified CLN2 precursor protein for 1, 2, 4 and 8 days. Cells were assayed for TPP-I activity. Data are expressed relative to the activity of a representative normal control human fibroblast cultured in the absence of recombinant CLN2 protein. The uptake increases as a function of time and concentration of exogenous enzyme added (FIG. 8). The activity assays indicate that relatively large amounts of CLN2 protein can be delivered to LINCL cells. After one day exposure to 10 nM or higher concentrations of CLN2 protein, the activity of the LINCL fibroblasts was equivalent to that of the normal control fibroblasts. After 8 days, intracellular accumulation of CLN2 protein exceeded that of the control fibroblasts by up to a factor of about 5. Note that the increase in activity over time indicates that the recombinant CLN2 protein is stable in culture media containing 10% FBS. Control experiments indicated that most if not all of the uptake occurred via mannose 6-phosphate receptor-mediated endocytosis (FIG. 8)

To determine the stability of the endocytosed enzyme, replicate wells of LINCL cells were grown for one day in complete medium containing recombinant CLN2 protein. The media were removed and replaced with complete medium. Wells were analyzed for TPP-I activity either immediately (day 0) or after an additional 1, 2, or 7 days of culture in the absence of exogenous CLN2 protein. The intracellular activity level was found to remain steady for at least 3 days and still maintained 70% of normal level 7 days after enzyme withdraw (FIG. 9). This indicates that the internalized CLN2 protein is quite stable, having a half-life of greater than one week.

Immunofluorescence analysis. We used confocal microscopy and immunofluorescence staining with anti-CLN2 protein antisera to determine the intracellular location of the recombinant CLN2 protein delivered to LINCL cells. When analyzing cells incubated with 32 nM CLN2 protein for one day, the staining pattern of LINCL fibroblasts was indistinguishable from that of normal fibroblasts (FIG. 10). The staining pattern is typical for lysosomal markers, indicating correct delivery of recombinant enzyme into the lysosomal compartment.

Uptake of CLN2 protein by cultured neurons. To determine the ability of the recombinant enzyme to be delivered to neurons, we cultured rat cerebellar granule neurons with increasing concentrations of CLN2 protein for one day and analyzed intracellular TPP-I activity using the kinetic assay.

Cerebellar granule neurons were prepared from postnatal day 8 Sprague-Dawley rat pups as described (Meiners, et al., (1999) J Neurosci 19, 8443-8453). The cells were plated into 48-well plates at a density of 150,000 cells/cm$^2$. When cells were confluent, media were replaced with fresh media containing the indicated concentrations of purified recombinant human CLN2 protein (0.5 ml). Immediately before processing, cells were washed 3 times with PBS (0.5 ml) at room temperature and then rapidly cooled by placing dishes in an ice water bath. The cells were lysed by adding 1% Nonidet P40/10 mM Tris pH 7.5/150 mM NaCl (0.2 ml/well) and incubated for 1 hour at 4° C. on a rocking platform. The lysate was transferred to microfuge tubes and centrifuged for 20 min at 13,000×g. The supernatant was used for enzyme activity and protein (Lowry, et al. (1951) J Biol Chem 193, 265-275) assays.

Depending on how the samples were processed (FIG. 12, legend), the TPP-I activity reflects either the mature CLN2 protein (triangles) or both precursor and mature CLN2 protein (circles) present within the neurons (FIG. 12). At concentrations of recombinant CLN2 protein where there was a significant increase of TPP-I activity over endogenous levels (>3 nM in the absence of M6P and >10 nM in the presence of M6P), thus allowing reliable estimation of the endocytosed protein, ~80% of the endocytosed CLN2 protein was in the mature form (FIG. 12). This indicates that the enzyme is targeted to an acidic intracellular compartment but that this process is slower or less efficient than in fibroblasts. Also, unlike fibroblasts, the uptake did not saturate at high CLN2 protein concentrations. However, the M6P inhibitable uptake was saturable (FIG. 12, inset. EC50 6-8 nM), indicating that at high concentrations, there was considerable uptake through MPR-independent mechanisms. Nonetheless, even when MPR-independent mechanisms predominated, ~80% of the endocytosed enzyme was converted to the active form, demonstrating proper lysosomal targeting of the recombinant CLN2 protein.

The results presented here indicate that the recombinant CLN2 protein is efficiently endocytosed by LINCL fibroblasts and targeted to lysosome. However, when considering enzyme replacement as a potential therapy for LINCL, it is important to demonstrate that the endocytosed enzyme is functionally equivalent to the native enzyme and can correct the biochemical phenotype of the disease. A biochemical hallmark for LINCL is accumulation of mitochondrial ATP synthase subunit c (subunit c) in lysosomes. We cultured LINCL fibroblasts in the presence or absence of CLN2 protein and determined the relative levels of subunit c by western blotting (FIG. 11). Enzyme treatment dramatically reduced subunit c to levels approaching that of unaffected control fibroblasts (FIG. 11), demonstrating that recombinant CLN2 protein can correct the metabolic defect in LINCL cells.

The above examples provide a production system for recombinant human CLN2 protein and demonstrate that this protein can be delivered to lysosomes of CLN2 protein-deficient LINCL fibroblasts and correct the metabolic defect. Similar CHO-based production systems have been used to produce large quantities of other lysosomal enzymes for protein characterization and enzyme replacement studies (Kakkis, et al. (1994) Protein Expr Purif 5, 225-232; Ioannou et al. (1992) J Cell Biol 119, 1137-1150; Bielicki, J., et al. (1998) Biochem J 329, 145-150; Martiniuk et al. (2000) Biochem Biophys Res Commun 276, 917-923). Consistent with our findings, overexpression of a given recombinant lysosomal enzyme typically results in its disproportionate secretion (Kakkis, Ioannou).

The properties of the CLN2 protein precursor differ in a number of aspects from that of the mature protein. First, the precursor is enzymatically inactive but, upon acidification, is autocatalytically processed to the mature, active form. Second, the mature enzyme is rapidly inactivated when incubated at 37° C. at neutral pH (Sohar et al. (1999) J Neurochem 73, 700-711; Vines, D. and Warburton, M. J. (1998) Biochim Biophys Acta 1384, 233-242.

In contrast, the proenzyme is stable at neutral pH (FIG. 4) and can subsequently be converted to the active form (FIG. 12). Finally, the quaternary structure and physical properties of the proenzyme and mature enzyme appear to be quite different. For instance, published procedures for purification of mature CLN2 protein/TPP-I from mammalian tissues utilize detergent to maintain the protein in solution (Vines and Warburton; Doebber et al. (1978) Endocrinology 103, 1794-1804; McDonald et al. (1985) Biochem Biophys Res Commun 126, 63-71; Watanabe et al. (1992) Biochem Int 27, 869-877; Page et al. (1993) Arch Biochem Biophys 306, 354-359; Junaid et al. (2000) J Neurochem 74, 287-294), and gel filtration analysis indicates that the mature protein forms aggregates of 250 to 700 KDa (McDonald et al.; Page et al.). In contrast, we show here that the proenzyme behaves as a soluble monomer.

Recombinant CLN2 protein produced from CHO cells has a number of properties that appear useful for enzyme replacement therapy in LINCL. First, as the proenzyme is inactive and stable in an extracellular environment until delivery to the lysosome, and the mature form is unstable with little activity at neutral pH, concerns about unwanted proteolysis of extracellular structures by TPP-I activity after enzyme administration should be minimized. Second, the protein is efficiently delivered to the lysosome by M6P mediated endocytosis (fibroblasts and neurons) and possibly by other endocytic mechanisms (neurons). Third, the endocytosed enzyme restores the deficient TPP-I activity of LINCL fibroblasts. Fourth, the internalized CLN2 protein can reverse a biochemical marker of the disease, i.e., storage of mitochondrial ATP synthase subunit c. Finally, the internalized active protein has a long half-life within lysosome, which will be important in considering dosing regimes.

Our results showed that large quantities of recombinant CLN2 protein can be readily obtained from our CHO cell system. This will facilitate enzyme replacement studies in animal models and development of novel delivery methods for treatment of LINCL.

All base sizes and amino acid sizes, and all molecular weight or molecular mass values given for nucleic acids or polypeptides are approximate, and are provided for description.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The contents of each reference, patent and patent application cited in this application is hereby incorporated by reference in its entirety.

The invention claimed is:

1. A method for treating a patient having disorder characterized by a deficient amount of functional tripeptidyl peptidase I (CLN2) protein in the affected cells, which comprises administering to the patient an amount of CLN2 protein comprising amino acids 20 to 563 of SEQ ID NO:1 effective to reduce or eliminate the symptoms caused by the deficiency in functional CLN2 protein.

2. A method of claim 1 wherein the disorder is characterized by accumulation of mitochondrial ATP synthase subunit c in the lysosomes of the affected cells.

3. A method of claim 2 wherein the affected cells are neuronal cells.

4. A method of claim 2 wherein the level of mitochondrial ATP synthase subunit c is reduced by administration of CLN2 protein.

5. A method of claim 3 wherein the disorder is late infantile neuronal ceroid lipofuscinosis (LINCL).

6. A method of claim 1 wherein the CLN2 protein is an inactive proenzyme.

7. A method of claim 6 wherein the CLN2 protein is a recombinant protein.

8. A method of claim 1 wherein the CLN2 protein is administered by injection.

9. A method of claim 1 wherein the CLN2 protein is administered with an uptake inhibitor, wherein the uptake inhibitor is mannose-6-phosphate.

10. A method of claim 8 wherein the effective amount of CLN2 protein is such that the affected cells receive from about 1.0 to about 100 nM of CLN2 protein.

11. A method of claim 9 wherein the effective amount of CLN2 protein is such that the affected cells receive from about 1.0 to about 100 nM of CLN2 protein.

12. A method for reducing the accumulation of mitochondrial ATP synthase subunit c in a subject having a disorder characterized by a deficiency in functional tripeptidyl peptidase I (CLN2) protein, comprising administering to the subject by intracranial injection an amount of CLN2 protein comprising amino acids 20 to 563 of SEQ ID NO:1, wherein said amount is effective to reduce the level of the mitochondrial ATP synthase subunit c in the neuronal cells of the subject.

13. The method of claim 12, wherein the disorder is late infantile neuronal ceroid lupofuscinosis (LINCL).

14. The method of claim 12, wherein the subject is a human.

15. The method of claim 12, wherein the CLN2 protein is an inactive proenzyme.

16. The method of claim 12, wherein the CLN2 protein is a recombinant protein.

17. The method of claim 12, wherein the CLN2 protein is administered with an uptake inhibitor, wherein said uptake inhibitor decreases local clearance of CLN2 protein by a cell surface receptor, and wherein said cell surface receptor is a mannose receptor, the asialoglycoprotein receptor or the mannose-6-phosphate receptor.

18. The method of claim 17, wherein the uptake inhibitor is mannose-6-phosphate.

19. The method of claim 12, wherein the effective amount of CLN2 protein is such that the neuronal cells receive from about 1.0 to about 100 nM of CLN2 protein.

* * * * *

UNITED STATES PATENT AND TRADEMARK OFFICE
CERTIFICATE OF CORRECTION

| | | |
|---|---|---|
| PATENT NO. | : 8,029,781 B2 | Page 1 of 1 |
| APPLICATION NO. | : 12/881066 | |
| DATED | : October 4, 2011 | |
| INVENTOR(S) | : Peter Lobel et al. | |

It is certified that error appears in the above-identified patent and that said Letters Patent is hereby corrected as shown below:

IN THE SPECIFICATIONS:

Column 1, line 18, insert the phrase --and NIH grant number NS037918-- after the phrase "NIDDK grant number D K 45992" to read:

--NIDDK grant number D K 45992, and NIH grant number NS037918--.

Signed and Sealed this
Sixth Day of November, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 563
<212> TYPE: PRT
<213> ORGANISM: Homo sapiens

<400> SEQUENCE: 1

Met Gly Leu Gln Ala Cys Leu Leu Gly Leu Phe Ala Leu Ile Leu Ser

-continued

```
  1               5                  10                 15
Gly Lys Cys Ser Tyr Ser Pro Glu Pro Asp Gln Arg Arg Thr Leu Pro
                    20                  25                  30

Pro Gly Trp Val Ser Leu Gly Arg Ala Asp Pro Glu Glu Glu Leu Ser
            35                  40                  45

Leu Thr Phe Ala Leu Arg Gln Gln Asn Val Glu Arg Leu Ser Glu Leu
 50                      55                  60

Val Gln Ala Val Ser Asp Pro Ser Ser Pro Gln Tyr Gly Lys Tyr Leu
 65                  70                  75                  80

Thr Leu Glu Asn Val Ala Asp Leu Val Arg Pro Ser Pro Leu Thr Leu
                85                  90                  95

His Thr Val Gln Lys Trp Leu Leu Ala Ala Gly Ala Gln Lys Cys His
                    100                 105                 110

Ser Val Ile Thr Gln Asp Phe Leu Thr Cys Trp Leu Ser Ile Arg Gln
            115                 120                 125

Ala Glu Leu Leu Leu Pro Gly Ala Glu Phe His His Tyr Val Gly Gly
        130                 135                 140

Pro Thr Glu Thr His Val Val Arg Ser Pro His Pro Tyr Gln Leu Pro
145                 150                 155                 160

Gln Ala Leu Ala Pro His Val Asp Phe Val Gly Gly Leu His His Phe
                    165                 170                 175

Pro Pro Thr Ser Ser Leu Arg Gln Arg Pro Glu Pro Gln Val Thr Gly
                180                 185                 190

Thr Val Gly Leu His Leu Gly Val Thr Pro Ser Val Ile Arg Lys Arg
                195                 200                 205

Tyr Asn Leu Thr Ser Gln Asp Val Gly Ser Gly Thr Ser Asn Asn Ser
210                 215                 220

Gln Ala Cys Ala Gln Phe Leu Glu Gln Tyr Phe His Asp Ser Asp Leu
225                 230                 235                 240

Ala Gln Phe Met Arg Leu Phe Gly Gly Asn Phe Ala His Gln Ala Ser
                    245                 250                 255

Val Ala Arg Val Val Gly Gln Gln Gly Arg Gly Arg Ala Gly Ile Glu
                260                 265                 270

Ala Ser Leu Asp Val Gln Tyr Leu Met Ser Ala Gly Ala Asn Ile Ser
            275                 280                 285

Thr Trp Val Tyr Ser Ser Pro Gly Arg His Glu Gly Gln Glu Pro Phe
        290                 295                 300

Leu Gln Trp Leu Met Leu Leu Ser Asn Glu Ser Ala Leu Pro His Val
305                 310                 315                 320

His Thr Val Ser Tyr Gly Asp Asp Glu Asp Ser Leu Ser Ser Ala Tyr
                    325                 330                 335

Ile Gln Arg Val Asn Thr Glu Leu Met Lys Ala Ala Ala Arg Gly Leu
                340                 345                 350

Thr Leu Leu Phe Ala Ser Gly Asp Ser Gly Ala Gly Cys Trp Ser Val
            355                 360                 365

Ser Gly Arg His Gln Phe Arg Pro Thr Phe Pro Ala Ser Ser Pro Tyr
        370                 375                 380

Val Thr Thr Val Gly Gly Thr Ser Phe Gln Glu Pro Phe Leu Ile Thr
385                 390                 395                 400

Asn Glu Ile Val Asp Tyr Ile Ser Gly Gly Phe Ser Asn Val Phe
                    405                 410                 415

Pro Arg Pro Ser Tyr Gln Glu Glu Ala Val Thr Lys Phe Leu Ser Ser
                420                 425                 430
```

```
Ser Pro His Leu Pro Pro Ser Ser Tyr Phe Asn Ala Ser Gly Arg Ala
        435             440             445
Tyr Pro Asp Val Ala Ala Leu Ser Asp Gly Tyr Trp Val Val Ser Asn
    450             455             460
Arg Val Pro Ile Pro Trp Val Ser Gly Thr Ser Ala Ser Thr Pro Val
465             470             475             480
Phe Gly Gly Ile Leu Ser Leu Ile Asn Glu His Arg Ile Leu Ser Gly
            485             490             495
Arg Pro Pro Leu Gly Phe Leu Asn Pro Arg Leu Tyr Gln Gln His Gly
            500             505             510
Ala Gly Leu Phe Asp Val Thr Arg Gly Cys His Glu Ser Cys Leu Asp
        515             520             525
Glu Glu Val Glu Gly Gln Gly Phe Cys Ser Gly Pro Gly Trp Asp Pro
        530             535             540
Val Thr Gly Trp Gly Thr Pro Asn Phe Pro Ala Leu Leu Lys Thr Leu
545             550             555             560
Leu Asn Pro
```